US006251342B1

United States Patent
Narula et al.

(10) Patent No.: US 6,251,342 B1
(45) Date of Patent: *Jun. 26, 2001

(54) FLUORESCENT FIBER OPTIC SENSOR ELEMENT FABRICATED USING SOL-GEL PROCESSING TECHNIQUES

(75) Inventors: Chaitanya Kumar Narula, Ann Arbor; Bennie Poindexter, Westland; Jeffrey Thomas Remillard, Ypsilanti; Willes Henry Weber, Ann Arbor, all of MI (US)

(73) Assignee: Ford Global Technologies, Inc., Dearborn, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/087,951

(22) Filed: Jun. 1, 1998

(51) Int. Cl.[7] .................................................. G01N 21/64
(52) U.S. Cl. ................ 422/82.07; 422/68.1; 422/82.05; 422/82.06; 422/82.08; 422/82.11; 422/83; 422/91
(58) Field of Search ............................. 422/82.06, 82.07, 422/82.08, 91, 82.11, 68.1, 83; 436/137, 172, 73; 427/243, 245, 246, 307, 309

(56) References Cited

U.S. PATENT DOCUMENTS

| 4,750,806 | 6/1988 | Biswas . | |
|---|---|---|---|
| 4,816,049 | 3/1989 | Hata et al. . | |
| 5,262,192 | 11/1993 | Nelson et al. . | |
| 5,489,988 | * 2/1996 | Ackley et al. | 422/82.11 |
| 5,490,490 | 2/1996 | Weber et al. . | |
| 5,589,396 | * 12/1996 | Frye et al. | 436/73 |
| 5,607,644 | 3/1997 | Olstein et al. . | |
| 5,637,507 | * 6/1997 | Wicks et al. | 436/166 |
| 5,650,311 | * 7/1997 | Avnir et al. | 435/176 |
| 5,653,777 | 8/1997 | Semerdjian . | |

OTHER PUBLICATIONS

Fluorescence characteristics of Cu–ZSM–5 zeolites in reactive gas mixtures: mechanisms for a fiber–optic–based gas sensor, Applied Optics, Jun. 1, 1997, vol. 46, No. 16, p. 3699–3707.

* cited by examiner

*Primary Examiner*—Jill Warden
*Assistant Examiner*—Dwayne K Handy
(74) *Attorney, Agent, or Firm*—Lorraine S. Melotik

(57) ABSTRACT

The invention is a fluorescent sensor element for detecting concentration changes of oxygen in an atmosphere suitable for high temperature applications such as automotive exhaust gases. It comprises an optical fiber, preferably silica, coated on at least a portion of its surface with a sol-gel processed porous uniform mixture of (1) matrix material of alumina, zirconia, titania, or silica or a mixture of any of them with (2) ceramic fluorescent indicator like Cu-ZSM-5 zeolite incorporated therein. In use of the sensor element in a system, a light source excites fluorescence in the indicator which is responsive to varying oxygen concentration in the contacted exhaust gas.

16 Claims, 2 Drawing Sheets

FLUORESCENT FIBER OPTIC SENSOR ELEMENT FABRICATED USING SOL-GEL PROCESSING TECHNIQUES

BACKGROUND OF THE INVENTION

1. Field of the Invention

The present invention is directed to an on-board gas composition sensor for monitoring oxygen content levels in the exhaust gas from an internal combustion engine. More particularly, the invention is related to an optic sensor element responsive to changing oxygen concentration and a process of making this element using sol-gel techniques whereby a fluorescent indicator is included in a metal oxide matrix.

2. Background of the Invention

Motor vehicle manufacturers use on-board gas sensors to measure exhaust gases for engine control purposes and for assessing the performance of a catalytic converter. Sensors of this type must be sufficiently robust to withstand the aggressive gases to which the sensor is exposed in an exhaust gas conduit and also the extreme conditions that exist there such as high temperatures (typically of about 500°–600° C.), temperature cycling, vibration, intermittent moisture, etc.

Exhaust gas sensors used to date are disadvantaged by the need for an electrical signal which varies in relation to the oxygen content level of the exhaust gas. The sensor output signal may be used as an input to an electronic engine control means, such as for an electronic engine control module controlling the air/fuel mixture which is fed at any given point in time to a combustion chamber of the engine. Maintaining the integrity of the electrical connections to the sensor presents a challenge in the field of motor vehicle engine control. In addition, a problem is presented in maintaining the correct functioning of the active sensor material exposed to the harsh environment of the exhaust conduit.

Recently issued U.S. Pat. No. 5,490,490 discloses a different type of oxygen sensor suitable for operation at exhaust gas temperatures of 400°–650° C. which is to overcome the disadvantages of such prior sensors. It employs a bead of porous inorganic oxide such as Cu-ZSM-5 zeolite fused to the end of a fiber-optic cable. The bead is exposed to exhaust gas and the cable is connected to a device consisting of a light source and fluorescence detector. Upon irradiation with ultraviolet or blue light (350–460 nm), the bead exhibits fluorescence whose intensity is related to either oxygen concentration or reductant to oxidant ratio of the exhaust gases. Attaching a bead to the end of the fiber, however, involves manufacturing complexity and using a bead provides an opportunity for it to be dislodged from the fiber during use. In addition, such a bead has high temperature durability issues, since a thermal expansion mismatch with the silica fiber might cause it to crack and fall off. It would be desirable to provide an optical fiber/fluorescent indicator element which has improved high temperature resistance, durability, and response time, which can be manufactured in a commercially desirable way.

The present invention provides such an element. These and other advantages of the invention will be understood from the following disclosure and detailed description of certain preferred embodiments.

SUMMARY OF THE INVENTION

A fluorescent oxygen sensor element useful at high temperatures is made using sol-gel techniques. The element comprises a gold-jacketed, optical fiber with a coating of, on at least a surface portion thereof, a substantially uniform mixture of metal oxide matrix material and ceramic fluorescent indicator material. The coating is deposited from a sol-solution mixture of (1) a metal oxide matrix forming material of at least one metal element selected from the group consisting of Si, Al, Ti, Zr or their mixture, and (2) ceramic fluorescent indicator material. Preferably the fiber is made of silica. The indicator is present in the coating in an amount of about 20 to 95%, by weight of the total coating, with higher concentration of this range being preferred. Preferably the forming material includes at least one metal alkoxide represented by the formula $M(OR)_n$ wherein R represents a lower alkyl group such as $CH_3$ or $C_4H_9$, M represents the metals disclosed above, and n is the valence of M.

The fluorescent indicator material may be any material that fluoresces when exposed to visible or ultraviolet light and whose fluorescence intensity changes when the gaseous environment around the material changes its oxygen or reductant concentrations. Examples of such material include, gamma-alumina, ceria, zirconia, titania, and copper ions incorporated in a matrix such as zeolite ZSM-5. The indicator material would be incorporated in the sol during processing prior to coating on the fiber.

Another aspect of the invention is the method of making the sensor element. The method includes first etching the silica cable surface to be coated with acid, and then coating the surface with a sol solution of the metal matrix material/indicator disclosed above, as by dipping the fiber into the sol. And then the sol coating is dried to form the element.

The current process advantageously provides a well adhering fluorescent indicator in a ceramic matrix onto an optic fiber. Further, it provides an extremely compact sensor element that can withstand the harsh and rugged environment of a vehicle exhaust system. And, the sensor element has improved response time over a "bead" sensor due to the intimate contact of the coating with the fiber surface.

DETAILED DESCRIPTION OF THE PREFERRED EMBODIMENTS

Figure 1:
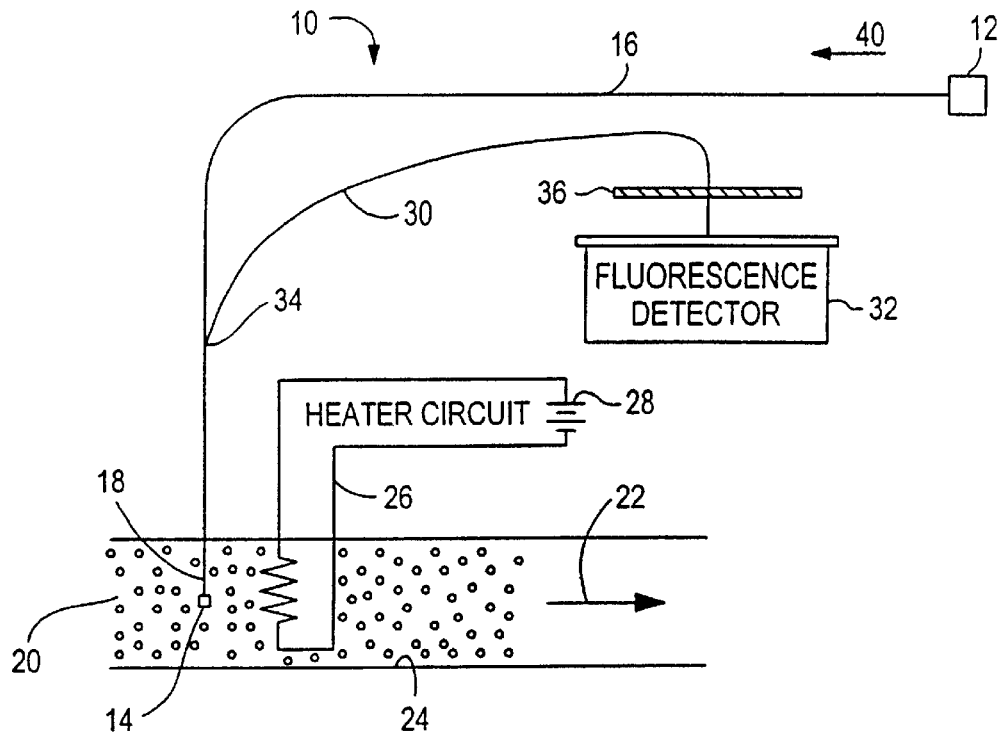
FIG. 1 is a schematic of a sensor system employing the present invention fiber optic sensor element.

It will be readily understood by those who are skilled in the art that there are numerous alternative designs for a sensor apparatus, one being shown in FIG. 1, which could suitably use the present invention sensor element. The apparatus is any that relies on the optical fluorescence signal from a porous element. The element of the present invention is particularly useful to monitor the gas composition in situ in the hot, corrosive motor vehicle exhaust gas environment. For example, the element is useful in a sensor system such as that of U.S. Pat. No. 5,490,490, the disclosure of which is hereby expressly incorporated by reference into this document. The invention sensor element may be used in other sensor systems, however, such as in a fixed power plant installation using a gaseous fuel (e.g., methane or propane) where accurate control of the air-to-fuel ratio is needed to optimize the fuel efficiency or minimize the emissions.

The on-board gas composition sensor system 10 schematically illustrated in FIG. 1, is seen to have a light source 12 for generating excitation light in the 350–525 nm wavelength range. Such an embodiment is taught in the above referenced patent application. Suitable light sources are commercially available and will be readily apparent to those skilled in the art in view of the present disclosure. Exemplary suitable light sources include laser diodes, light emitting diodes, and the like. Auxiliary focusing and filtering means are well known to those skilled in the art in view of the present disclosure.

The light from light source 12 is transmitted in the direction of arrow 40 to a sensor means comprising a sensor element 14 of a porous high-temperature fluorescent inorganic oxide ceramic coating 46 on a portion of fiber-optic cable 16, preferably at its end 18. Fiber-optic cable 16 should be adapted for high efficiency transmission of light in the 350–600 nm wavelength range and preferably is sufficiently robust for exposure at its distal end 18 to high temperatures and harsh environments as experienced in motor vehicle exhaust gas systems. Suitable fiber-optic cable which may be used in the present invention element is readily commercially available and includes fibers made from silica and germania, silica being most common. Still others useful in the present invention will be apparent to those skilled in the art in view of the present disclosure. The particular material of the cable and its thickness are not critical to the practice of this invention.

In use, ceramic coating 46 is seen to be exposed to exhaust gas 20, flowing in the direction of arrow 22 as it is passed to the atmosphere by exhaust gas conduit 24 of an internal combustion engine (not shown). The ceramic coating 46 will emit an optical fluorescence signal responsive to oxygen content in the exhaust gas 20, upon exposure of the ceramic coating 46 at a temperature typically in the range of 400°–600° C., to the excitation light carried to it by fiber-optic cable (excitation fiber) 16 from light source 12. The optical fluorescence signal generated by the sensor body 14 is carried back along the excitation fiber 16 to a fiber coupler 34, where it is coupled to another optical fiber 30, passed through a blocking filter 36 to remove the excitation light, and on to the fluorescence detector 32. The indicator phase fluoresces with an intensity that is related to the oxygen concentration or reductant to oxidant ratio of the exhaust gas.

Figure 2:
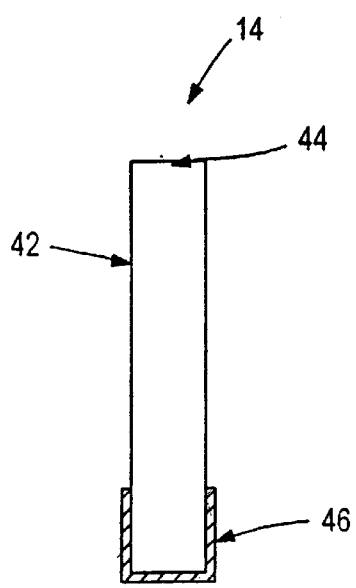
FIG. 2 is an expanded view of an embodiment of a present invention sensor element 14 shown in FIG. 1.

FIG. 2 shows an enlarged view of a present invention embodiment sensor element 14 fabricated as a coating 46 on a non-attached end of a 300μm all-silica, gold-jacketed fiber. A 25-mm section of protective gold jacket 42 was first removed from the fiber end using an acid etch. A silica sol was prepared by mixing silicon tetra-ethoxide, water, and nitric acid. The sol was aged for two weeks and then mixed with a small quantity of Cu-ZSM-5, as the indicator phase. Exposed fiber 44 was dipped in the slurry several times and allowed to dry in air. The drying of the coating 46 could also be hastened by exposure to elevated temperatures. While not wishing to be bound by theory, after complete drying, it is believed that chemical bonds are made from the coating 46 to the fiber at locations on the surface where there are residual hydroxyl (OH) groups. The thickness of the coating 46 can be controlled by the number of times the fiber 44 is dipped into the slurry. The thickness of the resultant coating is not critical to the practice of this invention, however, generally it would optimally be between 10 and 100 μm thick.

The porous coating can be deposited from any sol-solution mixture of metals selected from the group consisting of Si, Al, Ti, and Zr such as from metal salts such as halides, nitrates, alkoxides, the latter represented by formula $M(OR)_n$, wherein R represents a lower alkyl group, M represents a metal element selected from the group consisting of Si, Al, Ti and Zr, n being the valence of M. The preferred matrix forming materials are alumina and silica based, because these have good temperature characteristics and high gas-transport properties. The making of such sol-solutions is well known to those skilled in the art. In the case of alkoxides, it generally involves (1) acid or base catalyzed hydrolysis of metal alkoxides in water and/or parent alcohol or (2) modification of metal alkoxides with organics such as acetyl-acetone and subsequent hydrolysis or (3) direct hydrolysis in water and peptization in the presence of acid. In the case of nitrates or halides, it would be made by hydrolysis and subsequent peptization as is well known in the art of sol-gel coatings. Use of nitrates or halides has the drawback that salts are present.

Numerous suitable porous high-temperature fluorescent inorganic oxide ceramics are available for use as the fluorescent active material incorporated into the sol, which generally are expected to exist in suspension within the sol matrix material during processing. Such materials will be readily apparent to those skilled in the art in view of the present disclosure. Suitable fluorescent ceramics include ion-exchanged zeolites, such as copper bearing zeolites, e.g. commercially well known Cu-ZSM-5 zeolite, and other zeolites bearing typically about one percent by weight copper or other suitable metal ions. The ceramic fluorescent indicator material included in the sol may be copper or other metal ions contained within a matrix such as alumina, silica, titania, zirconia, ceria, or lanthana. The preferred fluorescent material is Cu-ZSM-5. While not wishing to be bound to theory, it is believed that the fluorescence comes from the $Cu^{1+}$ state and that the $Cu^{2+}$ state gives no fluorescence. The relative amounts of the two valence states depend on the gas to which the Cu-ZSM-5 is exposed. The oxidizing/reducing character of the gas thus can be inferred from the fluorescence signal, which is proportional to the concentration of the $Cu^{1+}$ state.

To form the sol mixture, generally it is preferred that 1–60% indicator is incorporated in the wet sol matrix mixture so that the resultant dried ceramic coating would preferably comprise about 20 to 95% indicator based on the total weight of the ceramic coating. The most preferred coating compositions of the present invention contain 30 to 60% indicator by total weight in a wet sol matrix which lead to 90–95% indicator based on total weight of resultant product (dried) coatings. The particular amount of indicator to be incorporated in the sol depends on such factors as the viscosity of sol, the viscosity of resulting slurry, and the durability of the resulting coating. Furthermore, it is preferable to keep the concentration of indicator in the higher amounts to obtain uniform coat of indicator on the fiber and provide higher fluorescence signal. Selection of the optimal amount of indicator included in the sol mixture would be within the skill of one skilled in the art in view of the present disclosure.

To form the coating on the fiber, the fiber surface to be coated is first subjected to an acid etch, generally with an acid like aqua regia in order to remove the protective jacket and prepare the surface to provide improved adhesion of the coating. Thereafter, the sol is provided onto the fiber surface, as by dipping or brushing, to the thickness desired. This may be accomplished by repeated coatings. The sol is then dried to produce the final coating of the element of the present invention. Drying may take place at room or elevated temperatures.

EXAMPLE 1

A silica sol was prepared by mixing silicon tetra-ethoxide (6.25 g), water (1.62 g), and nitric acid (0.13 ml of 1.0 M) in ethanol (41.56 ml) in a screw cap bottle. After aging two weeks, 0.3 g of Cu-ZSM-5 was mixed into the 1.0 g of sol to make a slurry.

EXAMPLE 2

In this example, two matrix sols are made according to embodiments of the present invention. Later, in another example herein, fluorescent material would be admixed therein prior to coating on a commercially available silica optical fiber.

A. Aluminum tris(sec-butoxide), (9.85 g) was added to distilled water (80 ml) at 80° C. with stirring. A white precipitate immediately formed which remained in suspension. The suspension was kept at 90° C. for one hour, and nitric acid (2.8 ml of 1.0 M) was added to the suspension. The alumina-sol so formed was boiled in an open flask to remove sec-butanol and peptized for 16 hours at 90° C.

B. 2,4-Pentanedione (6.54 g) was added to a freshly distilled suspension of aluminum tris(iso-propoxide), $Al(O^iPr)_3$, (6.5 g) in tetrahydrofuran (THF) (100 ml) and the reaction mixture was stirred overnight. The resulting solution was cooled to −78° C. and slowly reacted with water (1.72 g) mixed with THF (218 ml) while stirring. A clear solution 0.2 M based on $Al(O^iPr)_3$ was obtained.

EXAMPLE 3

Zirconium butoxide (2.0 g) and 2,4-pentanedione (1.41 g) were dissolve in isopropanol and allowed to react at room temperature. The reaction mixture was cooled to −79° C. and reacted with water (0.51 g) in isopropanol (15 ml). The sol thus formed was slowly warmed to room temperature and transferred to a screw cap bottle. Later, indicator material would be mixed therein to form the sol to be applied to the optical fiber.

EXAMPLE 4

Titanium isopropoxide (2.0 g) and 2,4-pentanedione (1.41 g) were dissolved in isopropanol and allowed to react at room temperature. The reaction mixture was cooled to −78° C. and reacted with water (0.51 g) in isopropanol (15 ml). The sol thus formed was slowly warmed to room temperature and transferred to a screw cap bottle. Indicator would be later mixed in to form a present invention embodiment mixture which could be applied to an optical fiber.

EXAMPLE 5

According to an embodiment of the present invention, a typical commercial, all-silica fiber-optic cable was coated with the Cu-ZSM-5 fluorescence indicator/silica sol medium prepared in Example 1, as shown in FIG. 1. More particularly:

1. A 25-mm section of protective jacket is removed from the end of a 300µm core, all-silica, gold-jacketed fiber using an aqua regia acid etch.

2. Silica sol (1.0 g) was used to make a slurry which was a substantially uniform mixture including 0.3 g of Cu-ZSM-5 indicator.

3. The exposed fiber end was dipped in the slurry several times and allowed to dry in air. The coating thickness can be increased by increasing the number of dip-coat-dry cycles.

Figure 3:
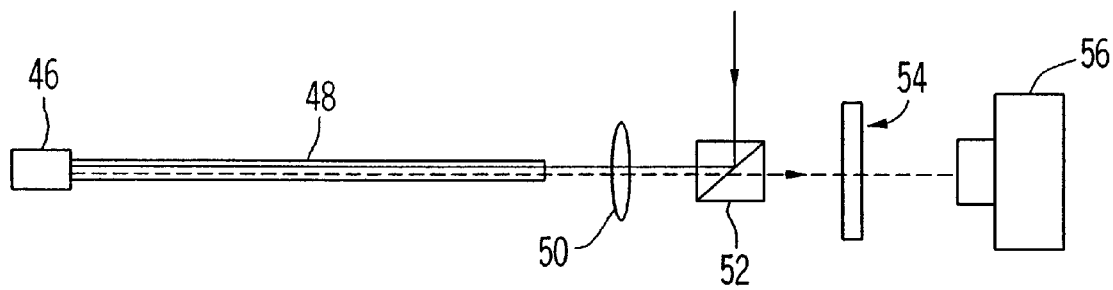
FIG. 3 is an optical schematic of a test system used to evaluate operation of the sensor element.

This product element was tested using the FIG. 3 evaluation system. The excitation source of the experiment was the 488-nm line of an argon-ion laser (indicated by the vertical arrow in FIG. 3), which was coupled into the fiber using a polarizing beamsplitter 52 and a microscope objective 50. The laser light propagates along the fiber 48 and excites a fluorescence signal in the coating 46 on the end of the fiber. A portion of the fluorescence signal propagates back along the same fiber, passes through the microscope objective, the beamsplitter, and a holographic filter 54 (to remove the excitation light), and then is focused onto a photomultiplier tube (PMT) 56. The signal from the PMT is thus proportional to the intensity of the fluorescence emitted by the fluorescent coating.

Figure 4:
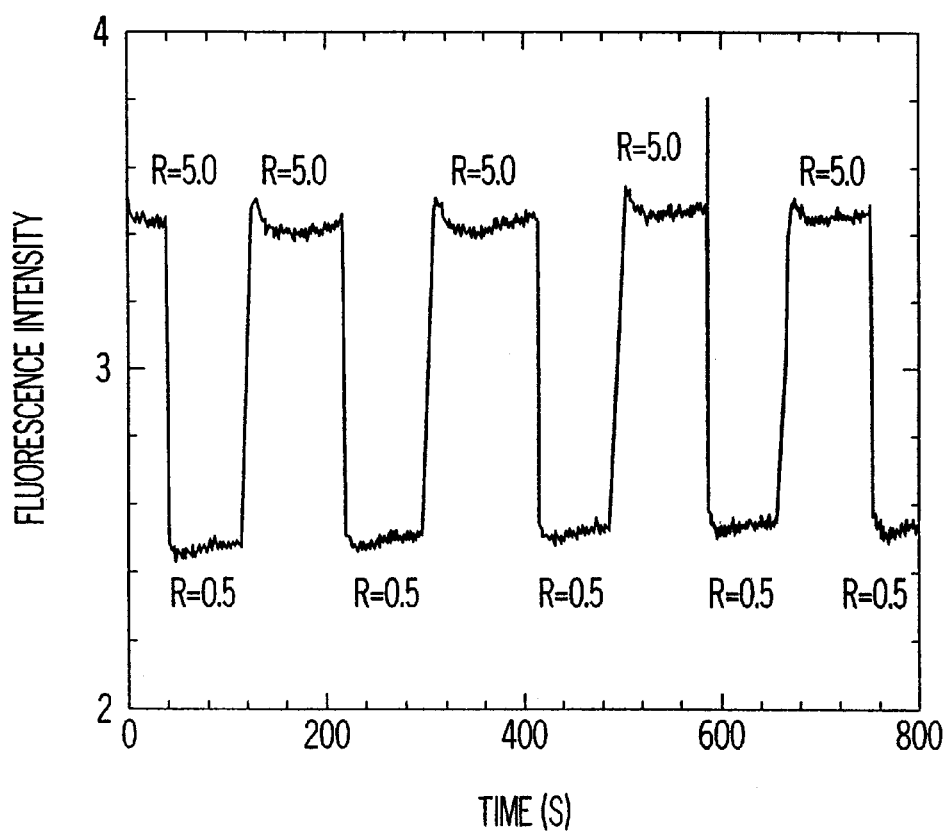
FIG. 4 shows the fluorescence intensity of an invention embodiment sensor element when exposed to changing $O_2$ concentration of a gas mixture, such that the R-value of the gas mixture switches from 5.0 to 0.5.

For the evaluation, the end of the fiber 18 containing the coating 46 was heated to 450° C. and exposed to a gas flow, particularly being $N_2$ containing 250 ppm of $C_3H_8$ (propane) and various concentrations of $O_2$. FIG. 4 shows the fluorescence intensity when the $O_2$ concentration is changed such that the R-value of the mixture switches from 5.0 to 0.5. (The R-value is proportional to the reductant-to-oxidant ratio of the gas, the constant of proportionality defined such that R=1 is a stoichiometric mixture for complete oxidation). As can be seen, when the R-value is decreased to 0.5 (i.e. when the oxygen concentration is increased) the fluorescence intensity decreases. This change in fluorescence intensity is reversible: when the R-value is increased to 5.0, the fluorescence intensity increases.

It will be obvious to those skilled in the art that various modifications may be made to the foregoing invention without departing from the spirit and scope of the following claims:

We claim:

1. A high temperature fluorescent oxygen sensor element for monitoring oxygen content in exhaust gas from an internal combustion engine made using sol-gel techniques and comprising an optical fiber carrying a coating of, on at least a surface portion thereof, a substantially uniform mixture of metal oxide matrix material and ceramic fluorescent indicator material, said coating being deposited from a sol-solution mixture of (1) a metal oxide matrix forming material of at least one metal selected from the group consisting of Si, Al, Ti, and Zr, and (2) ceramic fluorescent indicator material.

2. The sensor element according to claim 1, wherein the ceramic fluorescent indicator material is Cu-ZSM-5.

3. The sensor element according to claim 1, wherein the metal oxide matrix material is selected from nitrates, halides, and alkoxides of said metal elements.

4. The sensor element according to claim 3, wherein said alkoxide is represented by formula $M(OR)_n$ wherein R represents a lower alkyl group, M represents a metal of Si, Al, Ti, or Zr, and n is the valence of M.

5. The sensor element according to claim 4, wherein the sol is an alumina or silica sol.

6. The sensor element according to claim 1, wherein the ceramic fluorescent indicator material comprises metal ions contained in a matrix of alumina, silica, titania, ceria, lanthana, or zirconia.

7. The sensor element according to claim 1 wherein the coating includes about 20% to 95% indicator based on the total weight of said coating.

8. The sensor element according to claim 1 wherein the optical fiber is silica.

9. A method for making a high temperature fluorescent oxygen sensor element for monitoring oxygen content in exhaust gas from an internal combustion engine using sol-gel techniques, the steps comprising:

etching at least a portion of a surface of an optical fiber by acid etch;

coating the etched surface with a sol-gel solution comprising a substantially uniform mixture of (I) a metal oxide matrix forming material of at least one metal selected from the group consisting of Si, Al, Ti, and Zr, and (II) a ceramic fluorescent indicator material; and drying said sol to form a porous coating of a uniform mixture of metal oxide matrix and ceramic fluorescent indicator material.

10. The method according to claim 9, wherein the ceramic fluorescent indicator material is Cu-ZSM-5.

11. The method according to claim 9, wherein the metal oxide matrix material is selected from nitrates, halides and alkoxides of said metal elements.

12. The method according to claim 11, wherein said alkoxide is represented by the formula $M(OR)_n$, wherein R represents a lower alkyl group, M represents a metal of Si, Al, Ti, or Zr and n is the valence of M.

13. The method according to claim 12, wherein the sol is an alumina or a silica sol.

14. The method according to claim 9, wherein the ceramic fluorescent indicator material comprises metal ions contained in a matrix of alumina, silica, titania, zirconia, lanthana or ceria.

15. The method according to claim 9 wherein the coating includes about 20% to 95% indicator based on the total weight of said coating.

16. The method according to claim 9 wherein the optical fiber is made of silica.

* * * * *